United States Patent
Winkler

(10) Patent No.: US 6,251,673 B1
(45) Date of Patent: Jun. 26, 2001

(54) METHOD FOR MANUFACTURING AN IMPLANT CONSISTING OF A CARRIER MATERIAL CONTAINING MEDICALLY ACTIVE AGENTS

(75) Inventor: Heinz Winkler, Vienna (AT)

(73) Assignee: Mediphore-Biotechnologie AG, Vienna (AT)

( * ) Notice: Subject to any disclaimer, the term of this patent is extended or adjusted under 35 U.S.C. 154(b) by 0 days.

(21) Appl. No.: 09/254,555

(22) PCT Filed: Sep. 10, 1997

(86) PCT No.: PCT/AT97/00198

§ 371 Date: May 4, 1999

§ 102(e) Date: May 4, 1999

(87) PCT Pub. No.: WO98/10802

PCT Pub. Date: Mar. 19, 1998

(30) Foreign Application Priority Data

Sep. 10, 1996  (AU) .................................................. 1606/96

(51) Int. Cl.⁷ ...................................................... C12N 5/00
(52) U.S. Cl. .......................... 435/395; 435/403; 424/93.7
(58) Field of Search .................................... 435/395, 403; 424/93.7

(56) References Cited

U.S. PATENT DOCUMENTS 4,882,149 * 11/1989 Spector.
5,073,373 * 12/1991 O'Leary et al..
5,290,558 *  3/1994 O'Leary et al..

FOREIGN PATENT DOCUMENTS

0419275 A1 *  3/1991 (EP).

\* cited by examiner

*Primary Examiner*—Leon B. Lankford, Jr.
(74) *Attorney, Agent, or Firm*—Townsend and Townsend and Crew LLP

(57) ABSTRACT

The invention concerns an implant consisting of a carrier material containing medical substances such as pharmaceuticals, antibiotics, cytotstatic agents, hormones or the like made out of organic matter, preferably of a biological tissue of human, animal or plant origin, which before being incubated preferably in vacuum with one or the substances, is broken up, cleaned and freeze-dried.

20 Claims, No Drawings

METHOD FOR MANUFACTURING AN IMPLANT CONSISTING OF A CARRIER MATERIAL CONTAINING MEDICALLY ACTIVE AGENTS

BACKGROUND OF THE INVENTION

The invention relates to a method for manufacturing an implant consisting of a preferably adsorbable carrier material containing medically active agents such as pharmaceutical agents, antibiotics, cytostatics, hormones or the like.

In orthopedic operations, infections of the bone tissue (osteomyelitis) are common, which must be treated with antibiotics. Frequently, antibiotics administered intravenously or orally are without lasting therapeutic effect, even if the pathogen is susceptible. The reason is that the infected sectors are difficult to reach when the blood circulation is poor, when there is scar formation or sclerosis, and when there are membrane-like structures around the bacterial colonies which the antibiotics have difficulty penetrating. For that reason, it is inevitable that to control infections by means of intravenous or oral antibiotics, high doses must be administered on a long-term basis. However, there are limits to large doses due to the systemic side effects that may occur.

When infections occur in the bone tissue, a supplementary surgical intervention is therefore often necessary, in which all infected tissue sections are removed. Surgical debridement inevitably results in bone defects. To compensate for those, bone transplants are used, and this can cause numerous problems. Thus, bone transplants are primarily avital and therefore an ideal breeding ground for renewed bacterial invasion. As a rule, these bone transplants are therefore introduced only in a subsequent step, after the infection has been controlled. Otherwise there is a danger of sequestering the infection and making it persist.

It has therefore already been suggested to apply antibiotics locally in the infected area, but this has resulted in only partial success.

Local instillations are either too short in their effect or they require the application of time-consuming supply systems. At present, practically the only clinical method used consists of antibiotics carriers in the form of polymethylmetacrylate which are incubated with gentamycin. Other antibiotics can hardly be combined with such a carrier, which is reason enough for their limited use. The tissue levels reached are higher than with an intravenous or oral administration of antibiotics, but they are usually still insufficient for eliminating resistant germs. A substantial disadvantage of such antibiotics carriers is that they must be removed again after the patient has been at rest for a few days. To eliminate this disadvantage, some adsorbable implants have been developed very recently which consist of collagen sponges of animal origin, soaked in gentamycin. So far, this method cannot be used with other antibiotics, and such implants are also effective for a few days only.

In other forms of treatment, it is necessary that the implants deliver no or not only locally applied antibiotics, but also other medically active agents. Thus, transplants used to fill bone defects usually possess no osteoinductive potency, i.e. there is no stimulation for bone formation. For that reason, the defects cannot be induced to regenerate themselves. These transplants act only as spacers along which new endogenous tissue is supposed to form. It therefore seems useful to add factors which will stimulate bone regeneration. Some of these have already been identified, and some can even be produced by means of gene technology. However, problems persist in clinical applications, since such substances cannot be applied in a high-enough concentration and not long enough in the required place of activity.

In surgery involving malignant tumours, a high local concentration of cytostatics is desirable in certain cases. In such cases, it is particularly necessary to avoid systemic effects, since the resulting damage to organs can sometimes become life-threatening.

In the case of other active agents, too (hormones, pharmaceutical agents), it is sometimes desirable to produce either a locally limited or a long-term and continuous effect. These goals can be achieved through the implantation of suitable carriers with the desired active agent.

SUMMARY OF THE INVENTION

From U.S. Pat. No. 4,882,149 A, a carrier material is known which is air-dried at 100° C. after washing. Such a high temperature damages the molecular structures of the carrier material and causes it to wrinkle, by which the cavities of the carrier material, which are the determining factor for the effectiveness of the active agent to be absorbed/adsorbed, are so much reduced in size that only a small quantity of this active agent can be stored in the carrier material. If bone material is used as carrier material, such treatment results in glue, which cannot be absorbed/adsorbed at all by the active agents.

From EP 419 275 A1, a demineralized bone power is known with a medication as another component.

WO 86/07265 discloses an implant that consists of natural bone materials and adsorbed physiological substances such as an antibiotic.

It is an object of the present invention to suggest a method for manufacturing an implant which consists of a carrier material which is preferably adsorbable and with which a local application of medically active agents of many different kinds is made possible in variable doses over variable periods of time. To achieve this objective, it is suggested that an organic material forming the carrier material, in particular a biological tissue of human, animal or plant origin such as bone, sinew, muscle or the like, is comminuted, cleaned and freeze-dried, after which this carrier material is incubated with a solution containing the active agents. By means of such freeze-drying prior to incubation, the organic material forming the carrier material is prepared in such a way that on the one it is as dry as possible and therefore able to absorb/adsorb a very large amount of the active agent, and that on the other hand it is not damaged and completely retains its structures in the molecular as well as in the microscopic and macroscopic range. Such an implant manufactured in accordance with the method according to the invention therefore has the advantage that when the solution containing the effective agent is incubated, a very good enrichment according to its concentration gradient is ensured, whereby the complete rehydration of the freeze-dried material is achieved, and the effective agent is deposited in the organic material in an appropriately high dose, adsorbed and molecularly incorporated if necessary. By choosing the carrier material, the particle size, the concentration of the solution containing the active agent, and the incubation period, the effective intensity and the period of effectiveness of the active agent can be controlled and thus adapted to the requirements at hand.

It is already known that an implant can be freeze-dried after incubation. In this case, freeze-drying serves the purpose of making the implant imperishable, and since incubation of the carrier material occurs prior to freeze-drying, the latter has no effect of the behavior of the carrier material during incubation.

It stands to reason that after comminution, unwanted portions of the carrier material, such as tissue parts between the actual carrier structures (bone trabecula), should be removed, so that the enlarged contact areas result in better perfusion and increased adsorption of the solution containing the active agents.

The necessary cleaning of the organic material is done in a preferred step by means of a washing liquid that is preferably heated to a temperature between 40° and 60° C., which can be moved, for example by means of ultrasound and/or by shaking the vessel in which it is to be placed.

It is practical to subject the organic material, prior to freeze-drying, to fat removal by treating it with a fat-dissolving substance, such as ether. On the one hand, this increases the wettability of the surface of the organic material through the solution containing the active agent, and on the other hand, the ability of the organic material to absorb fatty or oily solutions is increased, which means that such fatty and oily solutions can also be stored in the carrier material to a large degree. Subsequently, the organic material can be treated with alcohol and then washed in sterilized water.

Finally, the organic material, after freeze-drying, can be subjected to ionizing radiation, which causes molecular changes in the organic material, resulting in better bonding with the active agent.

The freeze-dried material will be even better able to store the active agents if the freeze-dried material is incubated in a vacuum with a solution containing the active agent, since this means that the solution together with the dissolved active agents can penetrate the deepest structures of the carrier material without hindrance.

It has been shown that favorable results are obtained when the organic material is freeze-dried up to a residual moisture content below 10%, preferably below 5%.

A particularly gentle method of treating the carrier material is to freeze-dry it at a temperature between −20° and −40° C., preferably at −30° C.

DESCRIPTION OF THE PREFERRED EMBODIMENTS

The application of the method according to the invention is explained by means of an example. AMENDED SHEET Subsequently, the bone tissue is shaken for about two hours in the container of a mechanical shaker filled with washing water, at a frequency of between 50 and 100 Hz, after which the washing water is renewed, and the shaking operation is repeated at least once. The overall duration of this shaking and cleaning process is between four and eight hours.

Subsequently, the bone tissue is placed in a container filled with ether, which is shaken for at least three hours at a low frequency of about 60 Hz. This results in the removal of fat from the bone tissue. If this does not seem adequate after one run, the ether is renewed, and the process is repeated.

Subsequently, to elute the ether, the bone tissue is treated in shakers containing at first 70%, then 50% and finally 30% alcohol and subsequently sterilized water. The duration of each operation is approximately one to two hours.

The bone tissue thus prepared is now subjected to freeze-drying in suitable containers at a temperature of about −30° C. until it has a residual moisture of less than 5% (main drying process: pressure 0.370 bar, 0°, delta t minus 10°, 24 h; subsequent drying: 30 min.) and then stored in an evacuated, hermetically sealed container.

Following ionizing radiation of the bone tissue with a dose between 20 and 30 kgy, an aqueous or oily solution of the desired medically active agent, such as an antibiotic, is produced and incubated with the thus prepared bone tissue under vacuum. By varying the concentration of the solution, the duration of the incubation and the type and particle size of the carrier material, the amount of the active agent in the carrier material can be controlled. When this is applied, it results in defined and reproducible levels in the tissue to be treated or in the serum of the recipient.

Implantation can take place immediately after, but the produced implant may also by lyophilized, whereby only the moisture is extracted, while the active agent remains in the tissue. This ensures the almost unlimited durability and storability of the implant. In such a case, the agent is activated only directly prior to its use, by adding water, or only as soon as rehydration takes place after implantation through the body's own fluids. This depends on the diameter and density of the chosen carrier tissue, and it can therefore be maintained over time periods of variable length by selecting the carrier accordingly.

What is claimed is:

1. A method for manufacturing a medically active implant including a medically active agent comprising the steps of providing an organic material as a carrier material, comminuting the carrier material, cleaning the carrier material, freeze-drying the carrier material, thereafter combining the carrier material with the active agent, and incubating the carrier material and active agent.

2. A method according to claim 1 wherein the organic material comprises biological tissue.

3. A method according to claim 2 wherein the biological tissue is one of human, animal and plant tissue.

4. A method according to claim 1 wherein the medically active agent comprises a pharmaceutical agent.

5. A method according to claim 1 wherein the medically active agent comprises an antibiotic.

6. A method according to claim 1 wherein the medically active agent comprises cytostatics.

7. A method according to claim 1 wherein the medically active agent comprises a hormone.

8. A method according to claim 1 wherein the step of cleaning the organic material comprises washing the organic material with a liquid having a temperature between 40° C. and 60° C.

9. A method according to claim 8 including the step of placing the liquid in a vessel and subjecting the liquid in the vessel to at least one of ultrasound and shaking to thereby move the liquid in the vessel.

10. A method according to claim 1 including, prior to the step of freeze-drying, treating the organic material with a fat-dissolving substance to remove fat from the organic material.

11. A method according to claim 10 wherein the fat-dissolving substance is ether.

12. A method according to claim 10 including, following the treating step, subjecting the organic material to alcohol and thereafter washing the organic material with sterilized water.

13. A method according to claim 1 including the step of enlarging a surface of the organic material.

14. A method according to claim 13 wherein the step of enlarging comprises subjecting the organic material to ultrasound.

15. A method according to claim 1 including subjecting the organic material after freeze-drying to ionizing radiation.

16. A method according to claim 1 including subjecting the freeze-dried material and the active agent to a vacuum during the incubation step.

17. A method according to claim 1 wherein the freeze-drying step is carried out until the carrier material has a moisture content of less than 10%.

18. A method according to claim 17 wherein the carrier material is freeze-dried until it has a moisture content of no more than 5%.

19. A method according to claim 1 including the step of maintaining a temperature between $-20°$ C. and $-40°$ C. during the freeze-drying step.

20. A method according to claim 19 including maintaining the temperature during freeze-drying at $÷30°$ C.

* * * * *